(12) United States Patent
Cavendish

(10) Patent No.: US 8,746,241 B2
(45) Date of Patent: Jun. 10, 2014

(54) COMBINATION MDI AND NEBULIZER ADAPTER FOR A VENTILATOR SYSTEM

(76) Inventor: Sabrina B. Cavendish, Marengo, IN (US)

( * ) Notice: Subject to any disclaimer, the term of this patent is extended or adjusted under 35 U.S.C. 154(b) by 159 days.

(21) Appl. No.: 13/200,815

(22) Filed: Oct. 3, 2011

(65) Prior Publication Data

US 2013/0081617 A1  Apr. 4, 2013

(51) Int. Cl.
*A61M 15/00* (2006.01)
*A61M 16/10* (2006.01)
*A62B 9/04* (2006.01)

(52) U.S. Cl.
USPC .................................. 128/203.12; 128/202.27

(58) Field of Classification Search
USPC ............. 128/200.24, 202.27, 203.12, 200.14,
128/200.23, 204.18, 205.24, 207.14–207.16
See application file for complete search history.

(56) References Cited

U.S. PATENT DOCUMENTS

| | | | | |
|---|---|---|---|---|
| 4,951,661 | A * | 8/1990 | Sladek ...................... | 128/202.27 |
| 5,020,527 | A | 6/1991 | Dessertine | |
| 5,482,030 | A | 1/1996 | Klein | |
| 5,826,571 | A | 10/1998 | Casper et al. | |
| 5,848,587 | A | 12/1998 | King | |
| 5,996,579 | A | 12/1999 | Coates et al. | |
| 6,550,476 | B1 | 4/2003 | Ryder | |
| 6,588,421 | B1 | 7/2003 | Diehl et al. | |
| 7,069,928 | B1 | 7/2006 | Waldo et al. | |
| 7,204,245 | B2 | 4/2007 | Johnson et al. | |
| 7,207,329 | B2 | 4/2007 | Bowden | |
| 7,334,580 | B2 | 2/2008 | Smaldone et al. | |
| 7,360,541 | B2 | 4/2008 | Dhuper et al. | |
| 7,743,764 | B2 | 6/2010 | Dhuper et al. | |
| 7,841,342 | B2 | 11/2010 | Dhuper et al. | |
| 7,870,857 | B2 | 1/2011 | Dhuper et al. | |
| 2002/0073995 | A1 | 6/2002 | Rubin | |
| 2003/0226566 | A1 | 12/2003 | Dhuper et al. | |
| 2004/0011364 | A1 | 1/2004 | Dhuper et al. | |
| 2004/0089296 | A1 | 5/2004 | Bowden | |
| 2004/0123974 | A1 | 7/2004 | Marler et al. | |
| 2004/0234610 | A1 | 11/2004 | Hall et al. | |
| 2006/0283447 | A1 | 12/2006 | Dhuper et al. | |
| 2007/0169774 | A1 | 7/2007 | Johnson et al. | |
| 2007/0283954 | A1 | 12/2007 | Dhuper et al. | |
| 2008/0210242 | A1 | 9/2008 | Burk et al. | |
| 2008/0223361 | A1 | 9/2008 | Nieustad | |
| 2009/0288658 | A1 | 11/2009 | Charan et al. | |
| 2009/0301475 | A1 | 12/2009 | Korneff | |
| 2010/0078490 | A1 | 4/2010 | Fenlon | |
| 2010/0101566 | A1 | 4/2010 | Fenlon | |
| 2010/0139653 | A1 * | 6/2010 | Schloss .................... | 128/203.12 |
| 2010/0282253 | A1 | 11/2010 | Newman, Jr. | |

* cited by examiner

*Primary Examiner* — Kristen Matter
(74) *Attorney, Agent, or Firm* — Carrithers Law Office PLLC

(57) ABSTRACT

An improved medication introducing device for airtight connection in a ventilation circuit or similar emergency respiratory device, including an endo-tracheal tube, the device comprising a tubular manifold including an upstream opening, a downstream opening, a top opening for an MDI (metered dose inhaler) device connection and a bottom opening for a mini-nebulizer device connection. This system provides quick and easy to use ports in a one piece component for introduction of medications and drugs to patients for which an intravenous line cannot be established. The two ports include attached closures or caps to prevent contamination and are sized for friction fit connection of commonly used medication devices. The MDI port includes a toothed lug which operates a mechanical counter in the applicator head of an MDI device.

3 Claims, 3 Drawing Sheets

COMBINATION MDI AND NEBULIZER ADAPTER FOR A VENTILATOR SYSTEM

TECHNICAL FIELD

The present invention relates to the field of respiratory medication delivery systems and in particular, to a device which can be connected inline within a ventilator circuit and includes a top opening sized for air tight friction fit connection to an MDI (metered does inhaler) device and a bottom opening sized for air tight friction fit connection to a nebulizer device or a Mini-Neb nebulizer.

BACKGROUND OF THE INVENTION

A ventilator is a mechanical device which is used to provide help with breathing or to take over breathing altogether for a person incapable of doing so on his own. The ventilator provides compressed air or oxygen to the lungs and then allows the compressed air to escape at selected intervals continuously. This system may include a humidifier and heaters to condition the air for the patient and other devices such as a PEEP (positive end expiratory pressure parameter controlled with the ventilator.

It is often desirable or necessary to introduce medication or drugs such as ALBUTEROL, ATROVENT, FLOVENT, and PULMICORT to a patient who is already using a ventilator circuit or other breathing assist device. A preferred device used for this purpose is an MDI (metered dose inhaler) which typically comprises a small canister with the medication under pressure and a nozzle which can be pressed to release a dose of medication. Thus, the MDI is basically a compressed air canister filled with a combination of propellant and medication. This MDI device can be used with a housing which receives the canister and a mouthpiece whereby the patient inverts the canister and housing, puts the mouthpiece into his mouth and squeezes the canister down into the housing, causing the canister to inject the needed medication into the mouthpiece after which the patient inhales the medication directly into the lungs.

Further, another device called a nebulizer is used to introduce other medications, for example, asthma medication, into a patient's lungs. A nebulizer uses an electrical compressor to turn liquid medication into a fine mist for administering. A nebulizer is a small canister into which is placed a small amount of liquid medication, such as ALBUTEROL, ATROVENT, MYCOMYST, TOBRAMYCIN, MUCOMYST, PULMICORT and/or other antibiotics and drugs. Compressed air or oxygen is introduced into the liquid causing the liquid to become a mist which is easily breathed into the lungs.

It is often desirable to use an MDI device and/or a nebulizer within a ventilation system at any selected time. This would required the disassembly of the ventilator circuit and the connecting of either an MDI device adapter or a nebulizer adapter into the ventilator circuit. These adapters are connected inline with the already existing normal ventilator circuit and include a port for the temporary insertion of an MDI canister or a nebulizer device into the adapter and therefor, into the ventilator circuit. The disassembly of the ventilator circuit for this purpose is undesirable because of the possibility of introduction of contaminates and sources of infection and possible mistakes in re-assembly of the circuit. At present, MDI adapters and nebulizer adapters are individually available.

More recent MDI devices include a counter which counts each time the MDI device is pressed down so that a user will know that the device has been used a certain number of times, is nearly empty and needs to be replaced. An MDI device adapter which includes a longitudinal projection with teeth on one side to operate the counter operating gear is capable of operating the counter device within the MDI device. The integral longitudinal projection is near and parallel to the friction fit tube on the adapter which removably receives the MDI device nozzle. A metering valve controls the amount of the dose providing metered dose of medication delivered directly to the lungs via inhalation. A further addition to the adapter includes a removable cap which cover the opening for the MDI device while the MDI device is not connected, thus providing protection from contamination.

Adapters such as the MDI device adapter and the nebulizer adapter can be used in situations other than with a ventilator being used on a patient. For example these adapters can be used with a face mask type respirator or with a handheld respiratory device with a simple mouthpiece.

DESCRIPTION OF THE RELATED ART

U.S. Pat. No. 7,870,857 by Dhuper er al. for PATIENT INTERFACE ASSEMBLES FOR USE IN VENTILATOR SYSTEMS TO DELIVER MEDICATION TO A PATIENT which issued on Jan. 18, 2011 describes a ventilator system including a compressed air source, an inhalation valve, an exhalation valve, tubing, a humidifier, air heaters, tubing, a combination MDI and nebulizer adapter, a Y-connector, an electronic control system and an endotracheal tube. Dhuper does not describe the MDI and nebulizer adapter in significant detail or describe the specific connection details and is silent with respect to a counting device operator for the MDI device or the inclusion of a protective check valve on the nebulizer adapter portion.

US Patent Application Publication No. 20080223361 by Nieuwstad for RESPIRATORY MEDICINE DELIVERY SYSTEM which published on Sep. 18, 2008 describes a handheld respiratory medicine delivery device including a PEEP (positive end expiratory pressure) valve, an MDI adapter with a protective removable cap, a nebulizer adapter with a protective removable cap, and a mouthpiece. Also, Nieuwstad presents a combination of all the above which appears to be molded as a one piece unit. Nieuwstad is silent with respect to an MDI counting device operator member and to the sizing and connection details of tubular members of the combination and does not include a check valve in the nebulizer port.

US Patent Application Publication No. 20020073995 by Rubin for MULTIFUNCTION ORAL BREATHING SUPPORT SYSTEM which published on Jun. 20, 2002 describes a combination which includes a device for regulating how hard a patient must inhale to take in air, an MDI adapter, a nebulizer adapter, and a mouthpiece. Rubin is silent with respect to a one piece MDI/nebulizer adapter, to an MDI counting device operator and to the inclusion of a check valve in the nebulizer port.

Several embodiments of counters are available and useable with the present invention. For instance, U.S. Patent Publication 20100078490 by Felon for a "Metered-dose Inhaler" describes a rotary gear wheel counter"; U.S. Pat. No. 5,482,030 by Klein for an "Aerosol and Non-aerosol Spray Counter"; U.S. Pat. No. 5,826,571 by Casper et al. For a "Device for Use with Metered Dose Inhalers (MDIS)"; U.S. Pat. No. 5,020,527 by Dessertine for an "Inhaler device with Counter/Timer Means" and U.S. Patent publication 20100101566 by Felon for a "Metered-Dose Inhaler" all describe metered dose inhaler and counter mechanisms which can be used with the present invention and are hereby incorporated by reference in their entirety.

It is also contemplated that infrared or other sensing means could be utilized as a counter and used in combination with the adapter described by the instant invention.

SUMMARY OF THE INVENTION

In accordance with the present invention, there is provided a ventilator circuit for assisting with breathing or for performing the entire breathing function for a patient comprising an endotracheal tube connected to a Y-connector tube, with a first branch of the Y-connector tube being connected to an exhalation tube which is in turn connected to an exhalation solenoid valve, a second branch of the Y-connector tube being connected to a first inhalation tube which is in turn connected to an MDI/nebulizer adapter which is in turn connected to a second inhalation tube which is then connected to an inhalation solenoid valve. The inhalation valve and the exhalation valve are controlled by a ventilator system control unit which further includes a compressed air or oxygen source. The ventilator controller has control hardware capable of controlling breathing for the patient at a selected interval and selected flow rates. The MDI/nebulizer adapter includes a one piece generally longitudinal tubular housing including a downstream female connection end and an upstream male connection end. The upstream male connection end slightly tapers to a larger outer diameter going toward the downstream connection end of the adapter. The female connection end and the male connection end are capable of making a virtually air tight friction fit connection with connecting pieces of properly sized tubing. The tubular housing also includes an upper port for receiving an MDI (metered dose inhaler) canister with the upper port including a base with a vertical nozzle receiving tube extending upward from a center of the base. The nozzle receiving tube is in fluid communication with the tubular housing. The nozzle receiving tube has an inner diameter sized for an air tight friction fit with a nozzle of the MDI canister unit and the upper port also includes a vertical lug parallel with the vertical nozzle receiving tube. The lug includes teeth on one vertical edge which are capable of spinning a counter operating gear within a dose counter contained in a head piece on the canister and causing the counter to count down by one count when the canister is pressed down toward the base to dispense a dose of medication. The upper port also includes a first cap which is connected to the adapter by an first integral tether and is capable of tightly covering the nozzle receiving tube to prevent contamination when the MDI canister is not connected to the adapter. The tubular housing further includes a lower port for connecting a nebulizer into the ventilator circuit. The lower port has an inner diameter sized to receive and form an air tight friction fit with an upper end of a nebulizer. The nebulizer includes a bowl into which a selected amount of liquid medication is poured, a compressed air source, connecting tubing, and a misting nozzle. The air or oxygen is blown from the compressed air source through the connecting tube and the misting nozzle into the liquid medication contained within a bowl of the nebulizer causing the liquid medication to be converted into a mist which is then sucked through the lower port and into the ventilator circuit and on into a patient's lungs. The lower port includes a check valve which comprises a valve stem, a closure plate, a spring and a valve operator at the base of the valve stem. The check valve also has a stem aperture and a valve aperture. The check valve is forced open by the insertion of the nebulizer into the lower port. The check valve is held closed by the spring when the nebulizer is removed from the lower port. The lower port also contains a second cap capable of tightly closing the lower port when the nebulizer is unattached and is rotatably attached to the adapter by a second tether integral with the second cap. The upper and lower ports are separated from one another so as to prevent medication from one port from being deposited on the other port. The tubular housing further includes an integral loop providing a tie point which may be used to support or fix the adapter and attached ventilator circuit elements in a selected position relative to a patient.

It is an object of this invention to provide a combination ventilation circuit adapter which can be connected in-line with the inhalation tubing wherein the adapter includes and upper port for connecting an MDI device and a lower port for connecting a nebulizer device.

It is an object of this invention to provide a combination ventilation circuit adapter wherein the downstream connection end has diameter of approximately 22 mm and slightly tapers down for a friction fit to the downstream ventilation circuit tube and the upstream connection end has a diameter of 15 mm for friction fit into a upstream ventilation circuit tube.

It is an object of this invention to provide a combination ventilation circuit adapter wherein the upper port for an MDI device includes a vertical tube sized for a friction fit with a typical MDI aerosol canister nozzle and includes a vertical lug parallel to the vertical tube.

It is an object of this invention to provide a combination ventilation circuit adapter wherein the upper port for an MDI device includes a vertical tube sized for a friction fit with a typical MDI aerosol canister nozzle and includes a vertical lug parallel to the vertical tube. The lug includes teeth on one vertical edge for the purpose of operating a mechanical counter included in some MDI aerosol canister head pieces.

It is an object of this invention to provide a combination MDI/nebulizer circuit adapter wherein the lower port includes an integral check valve which seals off the lower port to the ventilator circuit when no nebulizer device is connected.

It is an object of this invention to provide a combination MDI/nebulizer circuit adapter wherein the lower port includes an opening with an inner diameter of approximately 18 mm, thus providing a friction fit with the connecting end of a nebulizer.

Other objects, features, and advantages of the invention will be apparent with the following detailed description taken in conjunction with the accompanying drawings showing a preferred embodiment of the invention.

BRIEF DESCRIPTION OF THE DRAWINGS

A better understanding of the present invention will be had upon reference to the following description in conjunction with the accompanying drawings in which like numerals refer to like parts throughout the views wherein.

DESCRIPTION OF THE PREFERRED EMBODIMENTS

Figure 1:
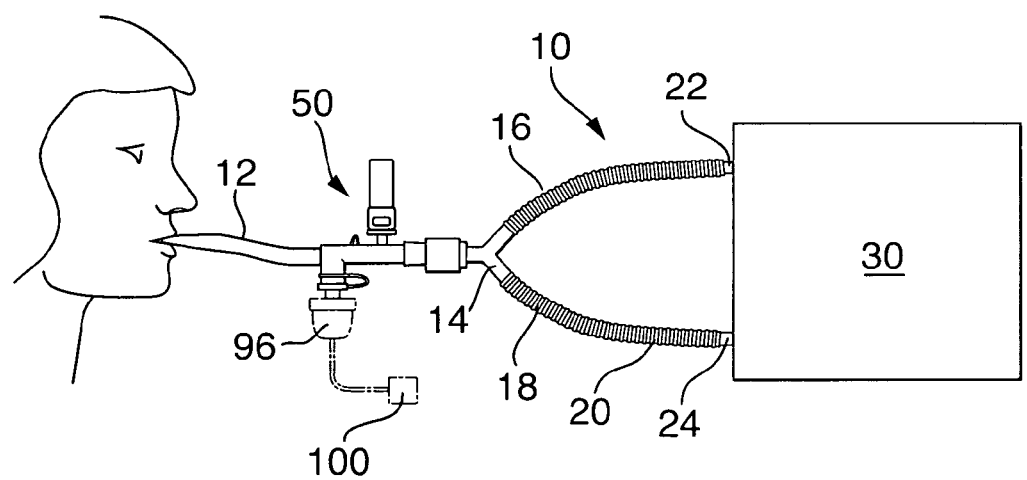
FIG. 1 is a ventilator system diagram including a ventilator control unit, various tubing and the MDI/nebulizer adapter of the present invention.

In accordance with the present invention, there is provided a combination MDI/nebulizer adapter for use in a ventilation circuit. FIG. 1 shows a simple ventilation circuit 10 including an endotracheal tube 12, a Y-connector tube 14, and exhalation tube 16 connected to an exhalation valve 22, an inhalation tube 18 connected to the MDI/nebulizer adapter 50 which is in turn connected to another inhalation tube 20, an inhalation valve 24 and a ventilator system control unit 30. Ventilator unit 30 contains a source for compressed air or oxygen and control hardware to maintain breathing for the patient at a selected interval and selected flow rates. More complex ventilator circuits may include a PEEP (positive end expiratory pressure parameter controlled with the ventilator), air or oxygen heaters and heater control circuitry, and a humidifier and control circuitry, for example, but have been omitted in this application for simplicity.

For purposes of discussion, the word 'downstream' refers to the direction toward the patient's mouth, which is the direction that medication introduced into the ventilator circuit travels. Therefore, the word 'upstream' refers to the direction away from the patient's mouth.

Figure 2:
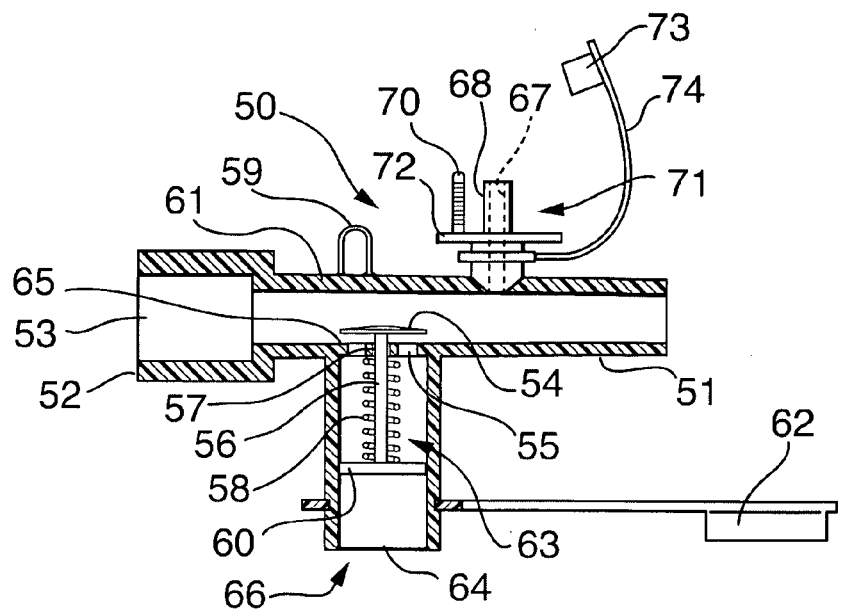
FIG. 2 is a side view of the combination MDI/nebulizer adapter.
Figure 3:
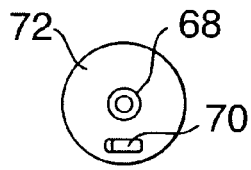
FIG. 3 is a top view of the MDI adapter.
Figure 4:
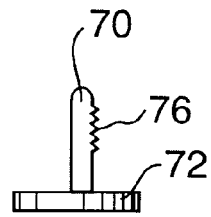
FIG. 4 is a side view of the MDI adapter showing the counter operating lug including teeth on one edge.

FIG. 2 shows the combined MDI/nebulizer adapter 50 of the present invention. Adapter 50 includes a generally longitudinal tubular housing 61 comprising a downstream connection end 52 with an inner diameter 53 of approximately 22 mm and an upstream connection end 51 with an outer diameter of approximately 15 mm and slightly tapering to a larger outer diameter going toward the downstream connection end 52 of the adapter 50 to enable a virtually air tight friction fit with a connecting piece of tubing. Adapter 50 is preferably translucent or clear to allow visual inspection of the internal portions of the housing and is typically constructed of thermoplastic compounds which are non-reactive with medications and bodily fluids.

Figure 5:
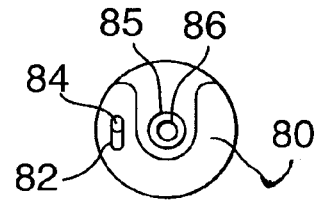
FIG. 5 is a top view of an MDI aerosol canister head piece showing the aperture through which the counter operating lug protrudes and a portion of the counter operating gear.
Figure 7:
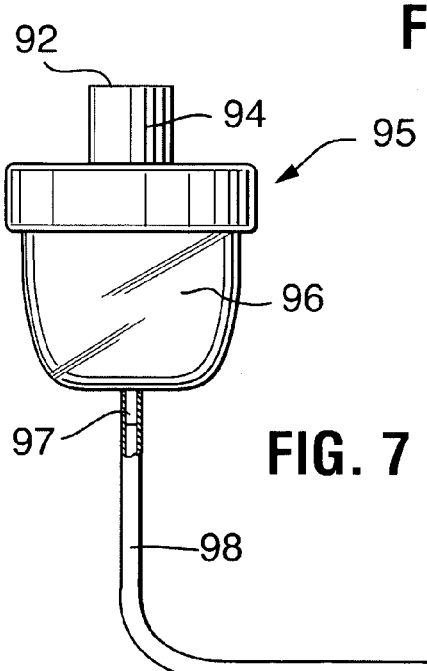
FIG. 7 is a front view of a nebulizer jet unit and compressed air supply.
Figure 6:
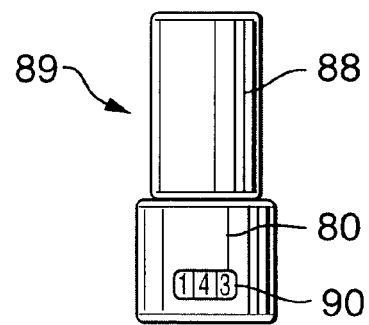
FIG. 6 is a front view of an MDI aerosol canister including a head piece and showing the mechanical counter display.
Figure 8:
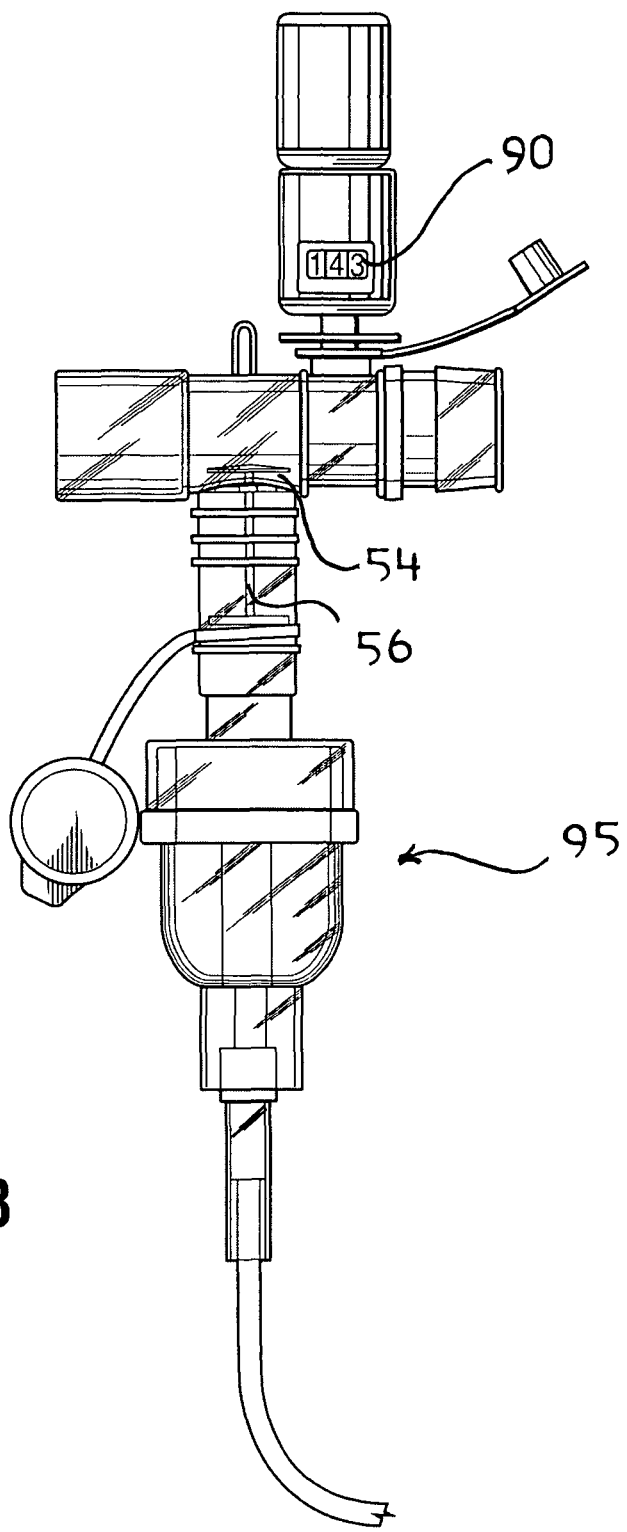
FIG. 8 is a front view of the adapter showing the MDI and nebulizer devices connected.

Adapter 50 further includes an upper port 71 for receiving an MDI canister 89 (shown in FIG. 6) and includes a base 72 with a vertical nozzle receiving tube 68 with an inner diameter 67 sized for an air tight friction fit with nozzle 86 of aerosol canister unit 89 shown in FIGS. 5 and 6. The preferred diameter of nozzle 86 is approximately 3 mm. The nozzle 86 is sized to slip into nozzle receiving tube 68 tightly. Upper port 71 also includes a vertical lug 70 with teeth on one vertical edge thereof. The teeth 70 cause gear 84, shown in FIG. 5, to spin when canister 89 is pressed downward to operate nozzle 86. As gear 84 spins, this action causes display counter 90 to count down by one count. Each time the aerosol canister 89 is depressed, the displayed count is decreased by one and when the display finally reads '000', this signifies to the user that the canister is empty and should be replaced. Also included with upper port 71 is a cap 73 which is rotatably connected to adapter 50 by an integral tether 74. Cap 73 is used to cover nozzle receiving tube 68 to prevent contamination when an MDI canister is not connected to adapter 50.

Adapter 50 further includes a lower port 66 for connecting a nebulizer 95 into the ventilator circuit 10. The inner diameter of aperture 64 of lower port 66 is sized to receive and form an air tight friction fit with the upper end 92 of nebulizer 95. The inner diameter 64 is preferably approximately 18 mm. Nebulizer 95 includes a bowl 96 into which a selected amount of liquid medication such as ALBUTEROL is poured. Air or oxygen is then blown from source 100 through tube 98 and nozzle 97 into the liquid medication contained within bowl 96 of nebulizer 95, thus causing the liquid medication to be converted into a mist which is passively provided as the ventilator cycles an inspiratory breath through port 66 and into the ventilator circuit and on into the patient's lungs. Port 66 includes a check valve 63 which comprises a valve stem 56, a stem aperture 57, a valve aperture 55, a closure plate 54, a valve seat 65, a spring 58 and a valve operator 60 at the base of valve stem 56. When there is no nebulizer inserted into port 66, check valve 63 closes to prevent contamination or ambient air from entering port 66. When nebulizer 95 is inserted into port 66, valve operator 60, stem 56 and closure plate 54 are is urged upward opening check valve 63 so that port 66 in now in fluid communication with nebulizer 95 and the nebulized medication may be drawn into the patient's lungs. A further protection from contamination for lower port 66 is provided by cap 62 which is rotatably connected to adapter 50 by tether 63.

As shown in FIG. 1, upper port 71 is not directly above lower port 66 for the purpose of preventing the deposit of medication from one port onto the other port. Preferably, lower port 66 is downstream of upper port 71 and the two ports are separated by at least 5 mm.

Adapter 50 is further provided with an integral loop 59 which provides a tie point which may be used to support or fix adapter 50 and the attached ventilator tubing in a selected position relative to a patient.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplification presented herein above. Rather, what is intended to be covered is within the spirit and scope of the appended claims.

I claim:

1. A ventilator circuit for assisting with breathing or for performing the entire breathing function for a patient consisting of:

an endotracheal tube connected to a Y-connector tube, a first branch of said Y-connector tube being connected to an exhalation tube which is in turn connected to an exhalation solenoid valve, said exhalation solenoid valve being connected to a ventilator system control unit, a second branch of said Y-connector tube being connected to a tube which is in turn connected to a metered dose inhaler (MDI)/nebulizer adapter which is in turn connected to a tube which is then connected to an inhalation solenoid valve, said inhalation solenoid valve and said exhalation solenoid valve being controlled by said ventilator system control unit which further includes a compressed air or oxygen source, said ventilator controller having control hardware capable of controlling breathing for the patient at a selected interval and selected flow rates by periodically opening and closing said solenoid valves;

said MDI/nebulizer adapter comprising a one piece generally longitudinal tubular housing including a downstream female connection end and an upstream male connection end, said upstream male connection end slightly tapering to a larger outer diameter going toward said downstream connection end of said adapter, said female connection end and said male connection end capable of making a virtually air tight friction fit connection with connecting pieces of properly sized tubing;

said tubular housing also including an upper port for receiving an MDI canister, said upper port including a base with a vertical nozzle receiving tube extending upward from a center of said base, said nozzle receiving tube being in fluid communication with said tubular housing, said nozzle receiving tube having an inner diameter sized for an air tight friction fit with a nozzle of said MDI canister, said upper port also including a vertical lug parallel to said vertical nozzle receiving tube, said lug including teeth on one vertical edge thereof, said teeth capable of spinning a counter operating gear within a dose counter contained in a head piece of said MDI canister and causing said counter to count down by one count when said canister is pressed down toward said base to dispense a dose of medication, said upper port also including a first cap being rotatably connected to said adapter by a first integral tether, said first cap being capable of tightly covering said nozzle receiving tube to prevent contamination when said MDI canister is not connected to said adapter;

said tubular housing further including a lower port for connecting a nebulizer into said ventilator circuit, said lower port having an inner diameter sized to receive and form an air tight friction fit with an upper end of the nebulizer, said nebulizer including a bowl into which a selected amount of liquid medication is poured, a compressed air source, connecting tubing, and a misting nozzle wherein air or oxygen is blown from said compressed air source through said connecting tubing and said misting nozzle into said liquid medication contained within the bowl of said nebulizer, thus causing said liquid medication to be converted into a mist which is then sucked through said lower port and into said ventilator circuit and on into a patient's lung during use, said lower port including a check valve which comprises a valve stem, a closure plate, a valve seat, a spring and a valve operator at a base of said valve stem, said check valve also having a stem aperture and a valve aperture formed therein, said check valve being forced open by the insertion of said nebulizer into said lower port and said check valve being held closed by said spring when said nebulizer is removed from said lower port, said lower port also containing a second cap capable of tightly closing said lower port when said nebulizer is unattached, said second cap being rotatably attached to said adapter by a second tether integral with said second cap;

said upper and lower ports being separated from one another so as to prevent medication from one port from being deposited on the other port said upper port positioned at a selected location other than directly above said lower port, said lower port positioned downstream of said upper port; and said tubular housing further including an integral loop providing a tie point which may be used to support or fix said adapter and attached ventilator circuit elements in a selected position relative to a patient.

2. A combination MDI (metered dose inhaler) and nebulizer adapter for a ventilator circuit, consisting of:

a one piece generally longitudinal tubular housing including a downstream female connection end and an upstream male connection end, said upstream male connection end slightly tapering to a larger outer diameter going toward said downstream connection end of said adapter, said female connection end and said male connection end capable of making a virtually air tight friction fit connection with connecting pieces of properly sized tubing;

said tubular housing also including an upper port for receiving an MDI canister, said upper port including a base with a vertical nozzle receiving tube extending upward from a center of said base, said nozzle receiving tube being in fluid communication with said tubular housing, said nozzle receiving tube having an inner diameter sized for an air tight friction fit with a nozzle of said MDI canister, said upper port also including a vertical lug parallel with said vertical nozzle receiving tube, said lug including teeth on one vertical edge thereof, said teeth capable of spinning a counter operating gear within a dose counter contained in a head piece of said canister and causing said counter to count down by one count when said canister is pressed down toward said base to dispense a dose of medication, said upper port also including a first cap being connected to said adapter by a first integral tether, said first cap being capable of tightly covering said nozzle receiving tube to prevent contamination when said MDI canister is not connected to said adapter, said tubular housing further including a lower port for connecting a nebulizer into said ventilator circuit, said lower port having an inner diameter sized to receive and form an air tight friction fit with an upper end of said nebulizer, said nebulizer including a bowl into which a selected amount of liquid medication is poured, a compressed air source, connecting tubing, and a misting nozzle wherein air or oxygen is blown from a compressed air source through said connecting tubing and said misting nozzle into said liquid medication contained within the bowl of said nebulizer, thus causing said liquid medication to be converted into a mist which is then sucked through said lower port and into said ventilator circuit and on into a patient's lung during use, said lower port including a check valve which comprises a valve stem, a closure plate, a valve seat, a spring and a valve operator at a base of said valve stem, said check valve also having a stem aperture and a valve aperture formed therein, said check valve being forced open by the insertion of said nebulizer into said lower port and said check valve being held closed by said spring when said nebulizer is removed from said lower port, said lower port also containing a second cap capable of tightly closing said lower port when said nebulizer is unattached, said second cap being rotatably attached to said adapter by a second tether integral with said second cap;

said upper and lower ports being separated from one another so as to prevent medication from one port from being deposited on the other port said upper port positioned at a selected location other than directly above said lower port said lower ort positioned downstream of said upper port; and said tubular housing further including an integral loop providing a tie point which may be used to support or fix said adapter and attached ventilator circuit elements in a selected position relative to said patient.

3. A ventilator circuit for assisting with breathing or for performing the entire breathing function for a patient consisting of:

an endotracheal tube connected to a Y-connector tube, a first branch of said Y-connector tube being connected to an exhalation tube which is in turn connected to an exhalation solenoid valve, said exhalation solenoid valve being connected to a ventilator system control unit, a second branch of said Y-connector tube being connected to a tube which is in turn connected to a metered dose inhaler (MDI)/nebulizer adapter which is in turn connected to a tube which is then connected to an inhalation solenoid valve, said inhalation solenoid valve and said exhalation solenoid valve being controlled by said ventilator system control unit which further includes a compressed air or oxygen source, said ventilator controller having control hardware capable of controlling breathing for the patient at a selected interval and selected flow rates by periodically opening and closing said solenoid valves;

said MDI/nebulizer adapter comprising a one piece generally longitudinal tubular housing including a downstream female connection end and an upstream male connection end, said upstream male connection end slightly tapering to a larger outer diameter going toward said downstream connection end of said adapter, said female connection end and said male connection end capable of making a virtually air tight friction fit connection with connecting pieces of properly sized tubing;

said tubular housing also including an upper port for receiving an MDI canister, said upper port including a base with a vertical nozzle receiving tube extending upward from a center of said base, said nozzle receiving tube being in fluid communication with said tubular housing, said nozzle receiving tube having an inner diameter sized for an air tight friction fit with a nozzle of said MDI canister, said upper port also including a vertical lug parallel to said vertical nozzle receiving tube, said lug including teeth on one vertical edge thereof, said teeth capable of spinning a counter operating gear within a dose counter contained in a head piece of said MDI canister and causing said counter to count down by one count when said canister is pressed down toward said base to dispense a dose of medication, said upper port also including a first cap being rotatably connected to said adapter by a first integral tether, said first cap being capable of tightly covering said nozzle receiving tube to prevent contamination when said MDI canister is not connected to said adapter;

said tubular housing further including a lower port for connecting a nebulizer into said ventilator circuit, said lower port having an inner diameter sized to receive and form an air tight friction fit with an upper end of the nebulizer, said nebulizer including a bowl into which a selected amount of liquid medication is poured, a compressed air source, connecting tubing, and a misting nozzle wherein air or oxygen is blown from said compressed air source through said connecting tubing and said misting nozzle into said liquid medication contained within the bowl of said nebulizer, thus causing said liquid medication to be converted into a mist which is then sucked through said lower port and into said ventilator circuit and on into a patient's lung during use, said lower port including a check valve which comprises a valve stem, a closure plate, a valve seat, a spring and a valve operator at a base of said valve stem, said check valve also having a stem aperture and a valve aperture formed therein, said check valve being forced open by the insertion of said nebulizer into said lower port and said check valve being held closed by said spring when said nebulizer is removed from said lower port, said lower port also containing a second cap capable of tightly closing said lower port when said nebulizer is unattached, said second cap being rotatably attached to said adapter by a second tether integral with said second cap;

said upper and lower ports being separated from one another so as to prevent medication from one port from being deposited on the other port, said upper port positioned at a selected location other than directly above said lower port, said lower port positioned downstream of said upper port and separated by at least 5 millimeters; and said tubular housing further including an integral loop providing a tie point which may be used to support or fix said adapter and attached ventilator circuit elements in a selected position relative to a patient.

* * * * *